United States Patent [19]

Okabe et al.

[11] 4,326,058
[45] Apr. 20, 1982

[54] ORGANO-PHOSPHORIC ESTERS AND THEIR PRODUCTION AND USE

[75] Inventors: Takayuki Okabe, Nishinomiya;. Masachika Hirano, Ibaraki; Kunio Mukai, Takarazuka, all of Japan

[73] Assignee: Sumitomo Chemical Company, Limited, Osaka, Japan

[21] Appl. No.: 116,214

[22] Filed: Jan. 28, 1980

[30] Foreign Application Priority Data

Feb. 5, 1979 [JP] Japan .................. 54-12496
Nov. 20, 1979 [JP] Japan ................. 54-151002

[51] Int. Cl.³ ................... C07F 9/65; C07D 239/36; A01N 57/16; A01N 57/32
[52] U.S. Cl. ..................... 544/243; 424/200; 544/319; 544/334
[58] Field of Search .................. 544/243; 424/200

[56] References Cited

U.S. PATENT DOCUMENTS

| | | | |
|---|---|---|---|
| 3,118,889 | 1/1964 | Schroeder | 544/242 |
| 3,243,437 | 3/1966 | Sherlock et al. | 544/243 |
| 3,328,405 | 6/1967 | Simone et al. | 544/243 |
| 3,384,540 | 5/1968 | Thomson et al. | 544/243 X |
| 4,014,996 | 3/1977 | Maurer et al. | 424/200 |
| 4,053,594 | 10/1977 | Riebel et al. | 424/200 |
| 4,113,860 | 9/1978 | Maurer et al. | 424/200 |

FOREIGN PATENT DOCUMENTS

64/24373 of 1964 Japan .

OTHER PUBLICATIONS

Shvachkin, et al., Chemical Abstracts, vol. 58, 9072f (1963).
Shvachkin, et al., Chemical Abstracts, vol. 61, 9576 (1964).
Sakamoto, et al., Heterocycles, 6, No. 5, pp. 525–529 (1977).
Schaefer, et al., J. Org. Chem., 26, pp. 412–418 (1961).
Oikawa, et al., J. Org. Chem., 43, pp. 2087–2088 (1978).
Kato, et al., Yakugaku Zasshi, 89 (4), pp. 460–463 (1969).
Collection of Lectures at Annual Meeting of Japan Pharmaceutical Association, vol. 2, p. 28 (1977).

*Primary Examiner*—Donald G. Daus
*Assistant Examiner*—Diana G. Rivers
*Attorney, Agent, or Firm*—Stevens, Davis, Miller & Mosher

[57] ABSTRACT

Phosphoro-thioates or dithioates of the formula (I),

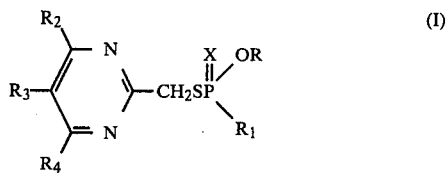

wherein R is a $C_1$–$C_3$ alkyl group, $R_1$ is a $C_1$–$C_3$ alkoxy, $C_1$–$C_4$ alkylamino or allylamino group, $R_2$ is a halogen atom, a $C_1$–$C_4$ alkoxy or $C_1$–$C_3$ alkyl group, $R_3$ is a hydrogen or halogen atom or a $C_1$–$C_3$ alkyl group, $R_4$ is a $C_1$–$C_3$ alkyl group, and X is an oxygen or sulfur atom, provided that when $R_1$ is a $C_1$–$C_4$ alkylamino or allylamino group, X is an oxygen atom, a process for producing phosphoro-thioates or dithioates of the formula (I) characterized by condensing a pyrimidine of the formula (II),

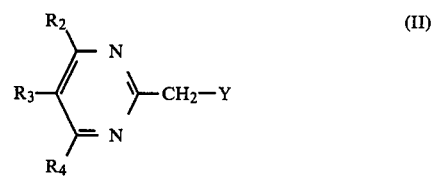

wherein Y is a halogen atom, and $R_2$, $R_3$ and $R_4$ are as defined above, with a thio- or dithio-phosphate of the formula,

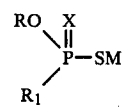

wherein M is an alkali metal atom or an ammonium group, and R, $R_1$ and X are as defined above, an insecticide, acaricide and nematocide characterized by containing phosphoro-thioates or dithioates of the formula (I) as an active ingredient, and pyrimidines, novel intermediate compounds, of the formula (II) wherein $R_2$ is a $C_1$–$C_4$ alkoxy group or a halogen atom, $R_3$ is a hydrogen or halogen atom or a $C_1$–$C_3$ alkyl group, and $R_4$ is a $C_2$–$C_3$ alkyl group.

7 Claims, No Drawings

ORGANO-PHOSPHORIC ESTERS AND THEIR PRODUCTION AND USE

The present invention relates to novel phosphoro-thioates or dithioates, their production and an insecticide, acaricide and nematocide compositions characterized by containing them as an active ingredient.

More particularly, the present invention relates to phosphoro-thioates or dithioates of the formula (I),

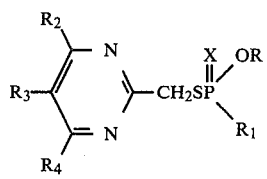

wherein R is a $C_1-C_3$ alkyl group, $R_1$ is a $C_1-C_3$ alkoxy, $C_1-C_4$ alkylamino or allylamino group, $R_2$ is a halogen atom, a $C_1-C_4$ alkoxy or $C_1-C_3$ alkyl group, $R_3$ is a hydrogen or halogen atom or a $C_1-C_3$ alkyl group, $R_4$ is a $C_1-C_3$ alkyl group, and X is an oxygen or sulfur atom, and a process for producing phosphoro-thioates or dithioates of the formula (I) characterized by condensing a pyrimidine of the formula (II),

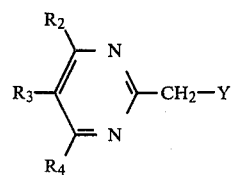

wherein Y is a halogen atom, and $R_2$, $R_3$ and $R_4$ are as defined above, with a thio- or dithio-phosphate of the formula (III),

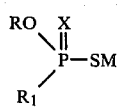

wherein M is an alkali metal atom (e.g. sodium, potassium) or an ammonium group, and R, $R_1$ and X are as defined above.

As the present compounds of the foregoing formula (I), the following examples will be shown hereinafter, but the present invention is not of course limited to these examples.

| Number | Structure | Physical constant |
|---|---|---|
| 1 | 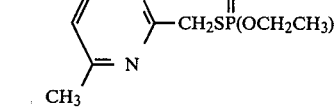 | $n_D^{20.0}$ 1.5649 |
| 2 | 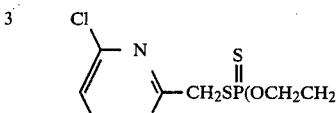 | $n_D^{20.0}$ 1.5570 |
| 3 | 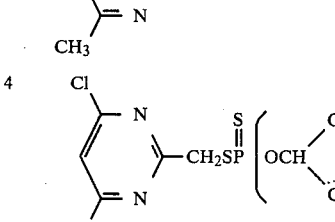 | $n_D^{26.0}$ 1.5434 |
| 4 | 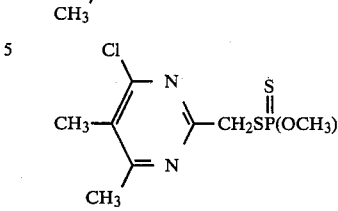 | $n_D^{20.0}$ 1.5426 |
| 5 | 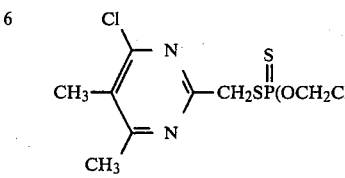 | $n_D^{21.7}$ 1.5518 |
| 6 | 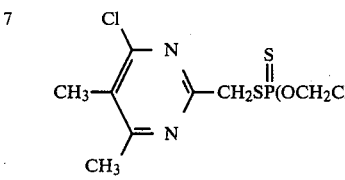 | $n_D^{21.7}$ 1.5340 |
| 7 | 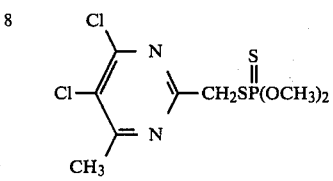 | $n_D^{19.0}$ 1.5512 |
| 8 | 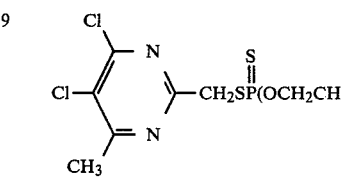 | $n_D^{19.5}$ 1.5492 |
| 9 | 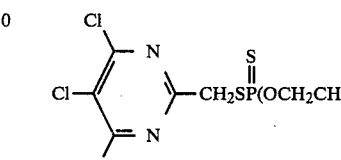 | $n_D^{20.0}$ 1.5478 |
| 10 | 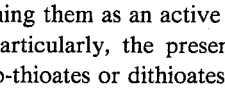 | $n_D^{20.5}$ 1.5325 |

| Number | Structure | Physical constant |
|---|---|---|
| 11 | CH₃O-[pyrimidine, CH₃]-CH₂SP(OCH₃)₂, S | $n_D^{19.0}$ 1.5600 |
| 12 | CH₃O-[pyrimidine, CH₃]-CH₂SP(OCH₂CH₃)₂, S | $n_D^{28.5}$ 1.5460 |
| 13 | CH₃CH₂O-[pyrimidine, CH₃]-CH₂SP(OCH₃)₂, S | $n_D^{25.0}$ 1.5422 |
| 14 | CH₃CH₂O-[pyrimidine, CH₃]-CH₂SP(OCH₂CH₃)₂, S | $n_D^{25.0}$ 1.5386 |
| 15 | CH₃CH₂CH₂O-[pyrimidine, CH₃]-CH₂SP(OCH₃)₂, S | $n_D^{25.0}$ 1.5426 |
| 16 | CH₃CH₂CH₂O-[pyrimidine, CH₃]-CH₂SP(OCH₂CH₃), S | $n_D^{25.0}$ 1.5379 |
| 17 | (CH₃)₂CHO-[pyrimidine]-CH₂SP(OCH₃)₂, S; CH₃ | $n_D^{27.0}$ 1.5399 |
| 18 | (H₃C)₂HCO-[pyrimidine, CH₃]-CH₂SP(OCH₂CH₃)₂, S | $n_D^{26.5}$ 1.5355 |
| 19 | CH₃CH₂CH₂CH₂O-[pyrimidine, CH₃]-CH₂SP(OCH₃)₂, S | $n_D^{27.0}$ 1.5379 |
| 20 | CH₃O-[pyrimidine, CH₃, CH₃]-CH₂SP(OCH₃)₂, S | $n_D^{26.0}$ 1.5500 |
| 21 | CH₃O-[pyrimidine, CH₃, CH₃]-CH₂SP(OCH₂CH₃)₂, S | $n_D^{26.0}$ 1.5430 |
| 22 | CH₃CH₂O-[pyrimidine, CH₃, CH₃]-CH₂SP(OCH₃)₂, S | $n_D^{26.0}$ 1.5426 |
| 23 | CH₃CH₂O-[pyrimidine, CH₃, CH₃]-CH₂SP(OCH₂CH₃)₂, S | $n_D^{26.0}$ 1.5386 |
| 24 | CH₃-[pyrimidine, CH₃]-CH₂SP(OCH₃)₂, S | $n_D^{17.5}$ 1.5592 |
| 25 | CH₃-[pyrimidine, CH₃]-CH₂SP(OCH₂CH₃)₂, S | $n_D^{18.0}$ 1.5510 |
| 26 | Cl-[pyrimidine, CH₃]-CH₂SP(OCH₃)₂, O | $n_D^{20.5}$ 1.5527 |
| 27 | Cl-[pyrimidine, CH₃]-CH₂SP(OCH₂CH₃)₂, O | $n_D^{20.0}$ 1.5452 |
| 28 | Cl-[pyrimidine, CH₃, CH₃]-CH₂SP(OCH₃)₂, O | $n_D^{20.0}$ 1.5398 |

| Number | Structure | Physical constant |
|---|---|---|
| 29 | 4-Cl, 5-CH3, 6-CH3-pyrimidin-2-yl-CH2SP(O)(OCH2CH3)2 | $n_D^{21.7}$ 1.5226 |
| 30 | 4,6-di(H3C)-pyrimidin-2-yl-CH2SP(O)(OCH3)2 | $n_D^{26.5}$ 1.5515 |
| 31 | 4,6-di(CH3)-pyrimidin-2-yl-CH2SP(O)(NHCH3)(OCH3) | $n_D^{26.5}$ 1.5429 |
| 32 | 4,6-di(CH3)-pyrimidin-2-yl-CH2SP(O)(NHCH2CH3)(OCH3) | $n_D^{26.5}$ 1.5378 |
| 33 | 4,6-di(CH3)-pyrimidin-2-yl-CH2SP(O)(NHCH2CH2CH3)(OCH3) | $n_D^{26.0}$ 1.5318 |
| 34 | 4,6-di(CH3)-pyrimidin-2-yl-CH2SP(O)(NHCH(CH3)2)(OCH3) | $n_D^{26.0}$ 1.5322 |
| 35 | 4,6-di(CH3)-pyrimidin-2-yl-CH2SP(O)(NHC4H9(n))(OCH3) | $n_D^{25.0}$ 1.5319 |
| 36 | 4,6-di(CH3)-pyrimidin-2-yl-CH2SP(O)(NHC4H9(iso))(OCH3) | $n_D^{25.0}$ 1.5303 |
| 37 | 4,6-di(CH3)-pyrimidin-2-yl-CH2SP(O)(NHC4H9(sec))(OCH3) | $n_D^{26.0}$ 1.5243 |
| 38 | 4,6-di(CH3)-pyrimidin-2-yl-CH2SP(O)(NHCH2CH=CH2)(OCH3) | $n_D^{26.0}$ 1.5462 |
| 39 | 4,6-di(CH3)-pyrimidin-2-yl-CH2SP(O)(NHCH3)(OCH2CH3) | $n_D^{25.0}$ 1.5313 |
| 40 | 4,6-di(CH3)-pyrimidin-2-yl-CH2SP(O)(NHCH2CH3)(OCH2CH3) | $n_D^{25.0}$ 1.5258 |
| 41 | 4,6-di(CH3)-pyrimidin-2-yl-CH2SP(O)(NHCH2CH2CH3)(OCH2CH3) | $n_D^{25.0}$ 1.5213 |
| 42 | 4,6-di(CH3)-pyrimidin-2-yl-CH2SP(O)(NHCH(CH3)2)(OCH2CH3) | $n_D^{25.5}$ 1.5221 |
| 43 | 4,6-di(CH3)-pyrimidin-2-yl-CH2SP(O)(NHC4H9(n))(OCH2CH3) | $n_D^{26.0}$ 1.5198 |
| 44 | 4,6-di(CH3)-pyrimidin-2-yl-CH2SP(O)(NHC4H9(iso))(OCH2CH3) | $n_D^{25.5}$ 1.5143 |
| 45 | 4,6-di(CH3)-pyrimidin-2-yl-CH2SP(O)(NHC4H9(sec))(OCH2CH3) | $n_D^{26.0}$ 1.5222 |
| 46 | 4,6-di(CH3)-pyrimidin-2-yl-CH2SP(O)(NHCH2CH=CH2)(OCH2CH3) | $n_D^{26.0}$ 1.5348 |

-continued

| Number | Structure | Physical constant |
|---|---|---|
| 47 | Cl, N, CH3, N, CH3, CH2SP(=O)(NHCH3)(OCH3) | $n_D^{24.5}$ 1.5348 |
| 48 | Cl, N, CH3, N, CH3, CH2SP(=O)(NHCH2CH3)(OCH3) | m.p. 57–59° C. |
| 49 | Cl, N, CH3, N, CH3, CH2SP(=O)(NHCH2CH2CH3)(OCH3) | $n_D^{26.0}$ 1.5342 |
| 50 | Cl, N, CH3, N, CH3, CH2SP(=O)(NHCH2i-C3H7CH3)(OCH3) | $n_D^{25.0}$ 1.5343 |
| 51 | Cl, N, CH3, N, CH3, CH2SP(=O)(NHCH2CH=CH2)(OCH3) | $n_D^{27.0}$ 1.5479 |
| 52 | Cl, N, CH3, N, CH3, CH2SP(=O)(NHCH3)(OCH2CH3) | $n_D^{24.5}$ 1.5442 |
| 53 | Cl, N, CH3, N, CH3, CH2SP(=O)(NHCH2CH3)(OCH2CH3) | $n_D^{25.0}$ 1.5405 |
| 54 | Cl, N, CH3, N, CH3, CH2SP(=O)(NHCH2CH2CH3)(OCH2CH3) | $n_D^{26.0}$ 1.5371 |
| 55 | Cl, N, CH3, N, CH3, CH2SP(=O)(NHC4H9(n))(OCH2CH3) | $n_D^{25.0}$ 1.5358 |
| 56 | Cl, CH3, N, CH3, N, CH2SP(=O)(NHCH3)(OCH3) | $n_D^{26.0}$ 1.5307 |
| 57 | Cl, CH3, N, CH3, N, CH2SP(=O)(NHCH2CH3)(OCH3) | $n_D^{26.0}$ 1.5271 |
| 58 | Cl, CH3, N, CH3, N, CH2SP(=O)(NHCH3)(OCH2CH3) | $n_D^{25.0}$ 1.5514 |
| 59 | Cl, CH3, N, CH3, N, CH2SP(=O)(NHCH2CH3)(OCH2CH3) | $n_D^{25.0}$ 1.5427 |
| 60 | Cl, Cl, N, CH3, N, CH2SP(=O)(NHCH3)(OCH3) | $n_D^{26.0}$ 1.5213 |
| 61 | Cl, Cl, N, CH3, N, CH2SP(=O)(NHCH2CH3)(OCH3) | $n_D^{26.0}$ 1.5165 |
| 62 | Cl, Cl, N, CH3, N, CH2SP(=O)(NHCH3)(OCH2CH3) | $n_D^{25.5}$ 1.5031 |
| 63 | Cl, Cl, N, CH3, N, CH2SP(=O)(NHCH2CH3)(OCH2CH3) | $n_D^{26.0}$ 1.4992 |
| 64 | Cl, N, CH3, N, CH2SP(=O)(OCH3)(OCH3) | $n_D^{24.0}$ 1.5664 |

| Number | Structure | Physical constant |
|---|---|---|
| 65 | 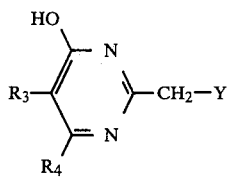 | $n_D^{24.0}$ 1.5467 |

The compounds of the present invention can be obtained with satisfactory results by reacting a pyrimidine (II) with a thio- or dithio-phosphate of the formula (III) in an amount of 1.0 to 1.3 times by mole based on the compound (II) at a temperature between 10° C. and 120° C. for 1 to 60 hours with stirring in a solvent. The solvent includes for example ketones (e.g. acetone, methyl isobutyl ketone), alcohols (e.g. methanol, ethanol), acetonitrile, benzene and toluene. After completion of the reaction, the objective compounds can be isolated by the common after-treatments, and if necessary they may further be purified, for example, by distillation or chromatography on silica gel.

Of the pyrimidines of the formula (II),

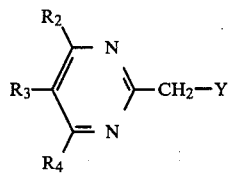   (II)

used as starting materials, those in which $R_2$ is a methyl group, $R_3$ is a hydrogen atom, $R_4$ is a methyl group and Y is as defined above, are well known and produced by the methods disclosed in the following literatures:

Yamanaka et al., Heterocycles, 6, 525 (1977)
Yamanaka et al., Collection of Lectures in the Japanese Pharmaceutical Meeting, Vol. 2, 28 (1977)

Of the pyrimidines of the foregoing formula (II), those in which $R_2$ is a halogen atom or a $C_1$-$C_4$ alkoxy group and $R_3$, $R_4$ and Y are as defined above, can be produced by the following methods.

(1) Pyrimidines of the formula (II'),

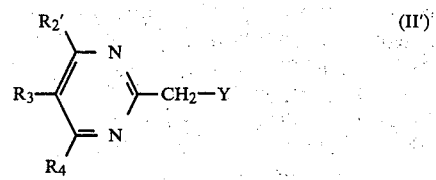   (II')

wherein $R_2'$ is a halogen atom and $R_3$, $R_4$ and Y are as defined above, can be produced by reacting a 4-hydroxypyrimidine of the following formula (II'') with phosphorus oxyhalide.

In this case, 4-hydroxypyrimidines of the formula (II''),

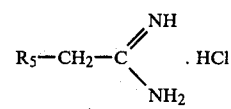   (II'')

wherein $R_3$, $R_4$ and Y are as defined above, are firstly produced by reacting an acetamidine hydrochloride of the formula (IV) [F. C. Shaefer et al.; J. Org. Chem., 26, 412 (1961)], $$R_5-CH_2-C\underset{NH_2}{\overset{NH}{\diagup}} \cdot HCl \quad (IV)$$

wherein $R_5$ is a halogen atom, with a β-ketoester of the formula (V) [O. Yonemitsu et al.; J. Org. Chem., 43, 2087 (1978)],

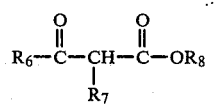   (V)

wherein $R_6$ is a $C_1$-$C_3$ alkyl group, $R_7$ is a hydrogen or halogen atom or a $C_1$-$C_3$ alkyl group, and $R_8$ is a $C_1$-$C_2$ alkyl group.

Referring now more particularly to this method, the objective 4-hydroxypyrimidines can be obtained as crystals in a high yield as follows: A mixture of a β-ketoester (V) (1 mole) and an acetamidine hydrochloride (IV) (1 to 1.5 mole) is dissolved in an alcohol (e.g. methanol, ethanol), water or a mixture thereof, and a 10 to 30% aqueous solution of sodium alcoholate (e.g. sodium methylate, sodium ethylate) or alkali hydroxide (e.g. sodium hydroxide, potassium hydroxide), the amount of the solution being 2 to 2.5 times by mole based on acetamidine hydrochloride (IV), is added thereto at 5° to 30° C. with stirring; the reaction mixture is stirred at 10° to 50° C. for 1 to 10 hours and concentrated under reduced pressure; the resulting dark brown solid residue is dissolved in water of 2 to 5 times by volume (v/v) based thereon, and the aqueous solution is adjusted to a pH of 4 to 6.5 with 6 N hydrochloric acid at 5° to 10° C., followed by extraction with chloroform, methylene chloride or methyl isobutyl ketone; and the organic layer is dried over anhydrous sodium sulfate and concentrated under reduced pressure to obtain the objective pyrimidines. Next, the pyrimidines of the formula (II') are obtained by halogenating the 4-hydroxypyrimidines of the formula (II'') thus obtained. That is, the objective pyrimidines can be produced in high purity and in high yield as follows: 4-hydroxypyrimidine of the formula (II'') is reacted with phosphorus oxyhalide (e.g. $POCl_3$, $POBr_3$) in an amount of 1.0 to 10.0 times by mole based on the 4-hydroxypyrimidine at 30° to 120° C. with stirring in the presence or absence of a solvent (e.g. benzene, toluene) inactive to phosphorus oxyhalide (the reaction comes to an end in 30 minutes to 2 hours); the solvent is removed by evaporation and the residue is dissolved in water, followed by extraction with an organic solvent; and the solvent is removed by evaporation, and the residue is distilled to obtain the objective pyrimidine.

(2) Pyrimidines of the formula (II'''),

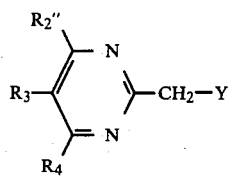

wherein $R_2''$ is a $C_1$-$C_4$ alkoxy group, and $R_3$, $R_4$ and Y are as defined above, can be obtained in a high yield as follows: A pyrimidine of the formula (II') obtained in (1) is reacted with sodium $C_1$-$C_4$ alcoholate in an amount of 1.0 to 1.5 times by mole based on (II') at 20° to 120° C. for 1 to 8 hours with stirring in the corresponding alcohol; the reaction solution is concentrated under reduced pressure, and the residue obtained is dissolved in benzene, followed by washing with water; the benzene layer is dried over anhydrous sodium sulfate and concentrated under reduced pressure; and the residue obtained is then distilled or column chromatographed to obtain the objective pyrimidine.

Some specific examples of the pyrimidines obtained by the methods (1) and (2) will be shown hereinafter.

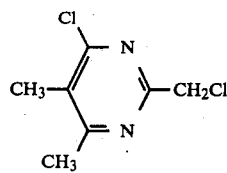 $n_D^{26.0}$ 1.5444

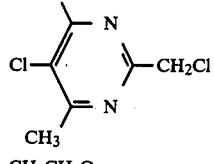 m.p. 42.0–43.5° C.

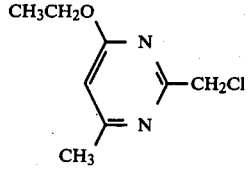 $n_D^{26.8}$ 1.5027

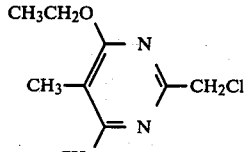 $n_D^{25.0}$ 1.5086

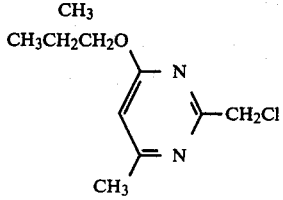 $n_D^{23.5}$ 1.5008

-continued

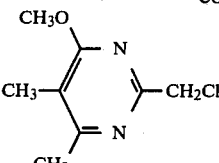 $n_D^{25.0}$ 1.5182

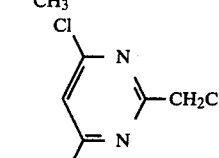 b.p. 73° C./ 0.13 mmHg

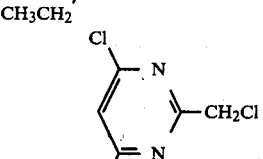 b.p. 87° C./ 0.27 mmHg

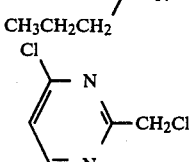 b.p. 73.5° C./ 0.1 mmHg $n_D^{20.0}$ 1.5405 (well known)

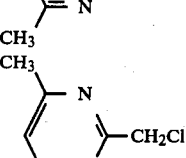 m.p. 72–73° C. (well known)

Of the pyrimidines represented by the formula (II), those in which $R_2$ is a $C_1$-$C_4$ alkoxy group or a halogen atom, $R_3$ is a hydrogen or halogen atom or a $C_1$-$C_3$ alkyl group and $R_4$ is a $C_2$-$C_3$ alkyl group, are novel compounds. Also, of 4-hydroxypyrimidines represented by the formula (II''), the one in which $R_3$ is a hydrogen atom, $R_4$ is a methyl group and Y is chlorine atom, is a well-known compound disclosed in Kato et al., Yakugaku Zasshi, 89, 460 (1969).

In the foregoing formulae, a halogen atom means a chlorine or bromine atom.

Some specific examples of a thio- or dithiophosphate of the formula (III), a starting material for the phosphoro-thioates or dithioates of the formula (I), will be shown hereinafter.

Sodium O,O-dimethyl phosphorodithioate
Sodium O,O-diethyl phosphorodithioate
Sodium O,O-di-n-propyl phosphorodithioate
Sodium O,O-di-isopropyl phosphorodithioate
Sodium O,O-dimethyl phosphorothioate
Sodium O,O-diethyl phosphorothioate
Sodium O,O-di-n-propyl phosphorothioate
Sodium O,O-di-isopropyl phosphorothioate As phosphoramidothioates, the following compounds may be given:
Sodium O-methyl N-methylphosphoramidothioate
Sodium O-methyl N-ethylphosphoramidothioate
Sodium O-methyl N-n-propylphosphoramidothioate
Sodium O-methyl N-isopropylphosphoramidothioate
Sodium O-methyl N-n-butylphosphoramidothioate
Sodium O-methyl N-isobutylphosphoramidothioate
Sodium O-methyl N-sec-butylphosphoramidothioate
Sodium O-ethyl N-methylphosphoramidothioate Sodium O-ethyl N-ethylphosphoramidothioate
Sodium O-ethyl N-n-propylphosphoramidothioate
Sodium O-ethyl N-isopropylphosphoramidothioate
Sodium O-ethyl N-n-butylphosphoramidothioate
Sodium O-ethyl N-isobutylphosphoramidothioate
Sodium O-ethyl N-sec-butylphosphoramidothioate
Corresponding potassium or ammonium salts Further, the present invention relates to an insecticide, acaricide and nematocide composition characterized by containing phosphorothioates or dithioates of the formula (I) as an active ingredient.

Insecticides, acaricides and nematocides have made a great contribution to a remarkable increase in agricultural production through their controlling effects against various harmful insects parasitic on agricultural crops. Various problems such as toxicity to mammals and pollution of natural environment have appeared and developed to such a situation that the use of these effective insecticides, acaricides and nematocides is feared in some fields.

For the reasons as described above, there is a strong demand for the development of insecticides, acaricides and nematocides which are low in toxicity, free from a fear of environmental pollution and effective in controlling various harmful insects.

As a result of an extensive study to develop excellent insecticides, acaricides and nematocides satisfying the above requirements, the inventors found that the present compounds of the formula (I) have properties meeting the above requirements, and thus completed the present invention. The combind insecticide, acaricide and nematocide of the present invention are particularly suitable for controlling stem-borers, planthoppers, leafhoppers and bugs in paddy field; insects doing damage to vegetables, fruit trees and wood, for example insects belonging to Lepidoptera [e.g. diamond-back moth (*Plutella xylostella*), armyworms and cutworms, tortorixes] and insects belonging to Orthoptera (e.g. grasshoppers); mites, nematodes, and disease-carrying mosquitoes, flies, cockroaches, ticks, fleas and lice; and insects harmful to stored cereals.

In the practical application of the present compounds, they may be applied alone without other components or in mixtures with carriers for the ease of use as controlling agents. The commonly used preparation forms, for example emulsifiable concentrates, wettable powders, dusts, granules, fine granules, heating fumigants, aerosols and baits, can be produced optionally, with no need of particular conditions like the common agricultural chemicals, by the methods well known to those skilled in the art. The compounds of the present invention can be applied to various usages in required preparation forms and with required carriers.

Further, multi-purpose compositions of excellent efficacy can be produced by mixing with other active ingredients, for example, oragano-phosphate insecticides such as O,O-dimethyl O-(3-methyl-4-nitrophenyl)phosphorothioate (hereinafter referred to as Fenitrothion) and O,O-dimethyl O-(2,2-dichlorvinyl)-phosphate (hereinafter referred to as DDVP); carbamate series insecticides such as 1-naphthyl N-methylcarbamate, 3,4-dimethylphenyl N-methylcarbamate and 3,5-dimethylphenyl N-methylcarbamate; pyrethriod series insecticides such as Allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin) and α-cyano-3-phenoxybenzyl 2-(4-chlorophenyl)isovalerate (hereinafter referred to as Fenvalerate); other insecticides, microbial pesticides such as fungicides, nematocides, acaricides, herbicides and B.T.; insect hormone compounds, other agricultural chemicals and fertilizers. Further, a synergistic effect can be expected by such mixing.

The preparations described above contain 0.1 to 95% by weight of the active ingredient (including other active ingredients mixed) in general.

The present invention will be illustrated in more detail with reference to the following examples and preparation examples.

EXAMPLE 1 (Compound No. 1)

4-Chloro-2-(chloromethyl)-6-methylpyrimidine (1.77 g, 0.010 mole), sodium O,O-dimethyl phosphorodithioate (2.0 g, 0.011 mole) and acetone (25 ml) were mixed and stirred for 15 hours at room temperature. The reaction mixture was poured into toluene (200 ml). The toluene solution was washed with water, and the toluene layer was dried over anhydrous sodium sulfate and concentrated under reduced pressure to obtain 2.96 g of a yellow oily residue. The residue was purified by column chromatography on silica gel to obtain 2.52 g of O,O-dimethyl S-(4-chloro-6-methylpyrimidin-2-ylmethyl)phosphorodithioate as a yellow oil (refractive index $n_D^{20.0}$ 1.5649).

Elementary analysis:

|  | C (%) | H (%) | N (%) |
|---|---|---|---|
| Calculated (as $C_8H_{12}ClN_2PS_2$) | 32.16 | 4.02 | 9.38 |
| Found | 32.31 | 4.01 | 9.53 |

$^1H$ NMR ($CCl_4$) δ6.95(s,1), 4.08(d,2), 3.75(d,6), 2.48(s,3).

EXAMPLE 2

(Compound No. 13)

2-(Chloromethyl)-4-ethoxy-6-methylpyrimidine (1.30 g, 0.007 mole), sodium O,O-dimethyl phosphorodithioate (1.45 g, 0.008 mole) and acetone (50 ml) were mixed and refluxed for 4 hours with stirring. The reaction solution was poured into toluene (200 ml). The toluene solution was washed with water, and the toluene layer was dried over anhydrous sodium sulfate and concentrated under reduced pressure to obtain 1.15 g of a yellow oily residue. The residue was purified by column chromatography on silica gel to obtain 0.82 g of O,O-dimethyl S-(4-ethoxy-6-methylpyrimidin-2-ylmethyl)-phosphorodithioate as a yellow oil (refractive index $n_D^{25.0}$ 1.5422).

Elementary analysis:

|  | C (%) | H (%) | N (%) |
|---|---|---|---|
| Calculated (as $C_{10}H_{17}N_2O_3PS_2$) | 38.96 | 5.52 | 9.09 |
| Found | 40.12 | 5.25 | 9.27 |

$^1H$ NMR ($CCl_4$) δ6.18(s,1), 4.30(q,2), 3.92(d,2), 3.65(d,6), 2.30(s,3), 1.33(t,3).

EXAMPLE 3

(Compound No. 31)

2-(Chloromethyl)-4,6-dimethylpyrimidine (1.57 g, 0.01 mole) and sodium O-methyl N-methylphosphoramidothioate (1.80 g, 0.011 mole) were dissolved in acetone (50 ml) and allowed to stand for 2 days. The reaction mixture was poured into toluene (200 ml). The toluene solution was washed with water, and the toluene layer was dried over anhydrous sodium sulfate and concentrated under reduced pressure to obtain 1.82 g of a yellow oily residue. The residue was purified by column chromatography on silica gel to obtain 1.30 g of O-methyl S-(4,6-dimethylpyrimidin-2-ylmethyl) N-methylphosphoramidothioate as a pale yellow oil (refractive index $n_D^{26.5}$ 1.5429).

Elementary analysis:

|  | C (%) | H (%) | N (%) |
| --- | --- | --- | --- |
| Calculated (as $C_9H_{16}N_3O_2PS$) | 41.38 | 6.13 | 16.09 |
| Found | 41.59 | 6.10 | 16.37 |

The compounds, Nos. (2) to (12), (14) to (30) and (32) to (65), were produced in the same manner as above.

The pyrimidine derivatives (II) used as starting materials were produced, for example, by the following methods.

EXAMPLE 4

[2-(Chloromethyl)-4-hydroxy-6-methylpyrimidine]

Chloroacetamidine hydrochloride (6.45 g, 0.05 mole), methyl acetoacetate (6.38 g, 0.055 mole) and 2 N aqueous sodium hydroxide solution (50 ml) were mixed and stirred for 1 hour at room temperature. The reaction solution was acidified (pH 4–5) with 6 N hydrochloric acid, followed by extraction with chloroform. The chloroform extract was dried over anhydrous sodium sulfate and concentrated under reduced pressure to obtain a brown crystal. The crystal was stirred in ether and then filtered to obtain 5.1 g (64% of the theoretical yield) of 2-(chloromethyl)-4-hydroxy-6-methylpyrimidine as colorless plate-like crystals (m.p. 157°–159° C.).

Elementary analysis:

|  | C (%) | H (%) | N (%) |
| --- | --- | --- | --- |
| Calculated (as $C_6H_7ClN_2O$) | 45.42 | 4.42 | 17.66 |
| Found | 45.70 | 4.38 | 17.71 |

The following compounds could be produced in the same manner as above.

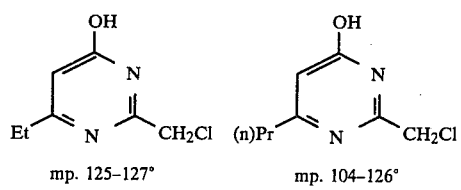

mp. 125-127°     mp. 104-126°

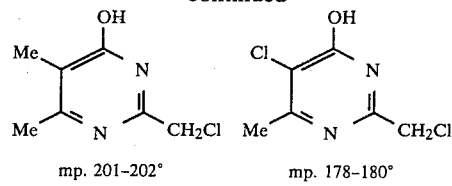

mp. 201-202°     mp. 178-180°

EXAMPLE 5

[4-Chloro-2-(chloromethyl)-6-methylpyrimidine]

A mixture of 2-(chloromethyl)-4-hydroxy-6-methylpyrimidine (10.0 g, 0.0565 mole) and phosphoryl chloride (30 ml) was stirred at 80° C. for 30 minutes. After cooling to room temperature, the reaction solution was concentrated under reduced pressure to obtain a black, oily residue. The residue was poured into ice water, followed by extraction with ether. The ether extract was washed with water, dried over anhydrous sodium sulfate and concentrated under reduced pressure to obtain 8.5 g of a dark yellow oily product. The product was purified by column chromatography on silica gel to obtain 6.3 g of 4-chloro-2-(chloromethyl)-6-methylpyrimidine as a yellow oil (refractive index $n_D^{20.0}$ 1.5405).

Elementary analysis:

|  | C (%) | H (%) | N (%) |
| --- | --- | --- | --- |
| Calculated (as $C_6H_6Cl_2N_2$) | 40.68 | 3.39 | 15.82 |
| Found | 40.65 | 3.31 | 15.68 |

EXAMPLE 6

[2-(Chloromethyl)-4-ethoxy-6-methylpyrimidine]

A solution of sodium ethylate (1.90 g, 0.028 mole) and 4-chloro-2-(chloromethyl)-6-methylpyrimidine (3.94 g, 0.02 mole) in ethanol (70 ml) was stirred for 3 hours at 50° C. After cooling to room temperature, the reaction solution was concentrated under reduced pressure to obtain a residue. The residue was dissolved in water (30 ml), followed by extraction with benzene. The benzene extract was washed with water, dried over anhydrous sodium sulfate and concentrated under reduced pressure to obtain 3.1 g of a yellow oily product. The product was purified by column chromatography on silica gel to obtain 1.30 g of 2-(2-(chloromethyl)-4-ethoxy-6-methylpyrimidine as a colorless oil (refractive index $n_D^{26.8}$ 1.5027) and 0.34 g of 4-ethoxy-2-(ethoxymethyl)-6-methylpyrimidine as a colorless oil (refractive index $n_D^{26.8}$ 1.4810).

Elementary analysis:

|  | C (%) | H (%) | N (%) |
| --- | --- | --- | --- |
| Calculated (as $C_8H_{11}ClN_2O$) | 51.47 | 5.90 | 15.01 |
| Found | 51.38 | 5.98 | 15.27 |

PREPARATION EXAMPLE 1

Fifty parts of each of the present compounds (1) to (65) is dissolved in 40 parts of xylene, and 10 parts of Sorpol SM-200, an emulsifier, (a registered trade mark of Toho Kagaku, Co., a mixture of an anionic surfactant and a nonionic one) is added thereto. The mixture is thoroughly stirred to obtain an emulsifiable concentrate of each compound.

PREPARATION EXAMPLE 2

Twenty parts of Fenitrothion (described above) is added to 20 parts of each of the present compounds (1), (2), (3), (5), (31), (32), (33), (35), (40) and (51), and then 50 parts of xylene and 10 parts of Sorpol SM-200 (described above) are added thereto. The mixture is thoroughly stirred to obtain an emulsifiable concentrate of each compound.

PREPARATION EXAMPLE 3

Forty parts of each of the present compounds (1) to (65) is well mixed with 5 parts of Sorpol SM-200 (described above), and 55 parts of 300-mesh diatomaceous earth is added thereto. The mixture is well mixed while being stirred in a mortar to obtain a wettable powder of each compound.

PREPARATION EXAMPLE 4

Three parts of each of the present compounds (1) to (65) is dissolved in 20 parts of acetone, and 97 parts of 300-mesh talc is added thereto. The mixture is thoroughly mixed while being stirred in a mortar, and acetone is then removed by evaporation to obtain a dust of each compound.

PREPARATION EXAMPLE 5

Two parts of 3-methylphenyl N-methylcarbamate is added to 2 parts of each of the present compounds (6), (7), (8), (9), (31), (42), (44) and (53), and the mixture is dissolved in 20 parts of acetone. After adding 96 parts of 300-mesh talc thereto, the mixture is treated in the same manner as in Preparation Example 4 to obtain a dust of each compound.

PREPARATION EXAMPLE 6

To 3 parts of each of the present compounds (1) to (65) are added 5 parts of Toyolignin CT (a salt of ligno-sulfonic acid, a registered trade mark of Toyo Spinning Co.) and 92 parts of GSM Clay (a registered trade mark of Zieklite Mining Co.), and the mixture is well mixed while being stirred in a mortar. Thereafter, the mixture is well mixed with water of 10% based thereon, granulated by means of a granulator and air dried to obtain a granule of each compound.

PREPARATION EXAMPLE 7

To 3 parts of each of the present compounds (1) to (65) are added 5 parts of Toyolignin CT (described above) and 92 parts of GSM Clay (described above), and the mixture is well mixed while being stirred in a mortar. Thereafter, the mixture is well mixed with water of 10% based thereon, granulated by means of a granulator for fine granule production and air dried to obtain a fine granule of each compound.

PREPARATION EXAMPLE 8

0.2 Part of each of the present compounds (1) to (65) is dissolved in kerosene and made up to 100 parts with kerosene to obtain an oil spray of each compound.

PREPARATION EXAMPLE 9

0.1 Part of tetramethrin is added to 0.2 part of each of the present compounds (25) and (52), and the mixture is dissolved in kerosene and made up to 100 parts with kerosene to obtain an oil spray of each compound.

PREPARATION EXAMPLE 10

0.2 Part of each of the present compounds (1) and (47), 0.2 part of (+)-trans-Allethrin, 7 parts of xylene and 7.6 parts of deodorized kerosene are well mixed to make a solution. The solution is filled in an aerosol container. After attaching a valve portion to the container, 85 parts of a propellant (liquefied petroleum gas) is charged therein under pressure through the valve to obtain an aerosol of each compound.

PREPARATION EXAMPLE 11

0.2 Part of each of the present compounds (5) and (31), 0.1 part of tetramethrin, 11.7 parts of deodorized kerosene and 1 part of Atmos 300, an emulsifier, (a registered trade mark of Atlas Chemical Co., monoglyceride series emulsifier) are mixed. The mixture is then emulsified with addition of 50 parts of pure water. The emulsion is then filled in an aerosol container together with 37 parts of a 3:1 mixture of deodorized butane and deodorized propane to obtain a water-based aerosol of each compound.

PREPARATION EXAMPLE 12

Eighty parts of each of the present compounds (1) to (65) is dissolved in 10 parts of xylene, and 10 parts of Sorpol SM-200, an emulsifier, (a registered trade mark of Toho Kagaku Co., a mixture of an anionic surfactant and a nonionic one) is added thereto. The mixture is thoroughly stirred to obtain an emulsifiable concentrate of each compound.

EXAMPLE 7

The emulsifiable concentrate obtained in Preparation Example 1 was diluted 1000 times with water (corresponding to 500 ppm of the active ingredient). On the bottom of a polyethylene cup of 5.5 cm in diameter was placed a piece of filter paper of the same size, and 0.7 ml of the above dilute liquor was dropped on the filter paper. Sucrose (30 mg) was placed on the paper as bait. Thereafter, 10 housefly female adults (*Musca domestica*) were liberated in the cup which was then covered with a lid. After 48 hours, the dead and alive were counted to obtain mortality (2 replications).

| Test compound | Mortality (%) | Test compound | Mortality (%) |
|---|---|---|---|
| (1) | 100 | (2) | 100 |
| (3) | 100 | (4) | 100 |
| (5) | 100 | (6) | 100 |
| (7) | 100 | (8) | 100 |
| (9) | 100 | (10) | 100 |
| (11) | 100 | (12) | 100 |
| (13) | 100 | (14) | 100 |
| (15) | 100 | (16) | 100 |
| (17) | 100 | (18) | 100 |
| (19) | 100 | (20) | 100 |
| (21) | 100 | (22) | 100 |
| (23) | 100 | (24) | 100 |
| (25) | 100 | (26) | 100 |
| (27) | 100 | (28) | 100 |
| (29) | 100 | (30) | 100 |
| (31) | 100 | (32) | 100 |
| (33) | 100 | (34) | 100 |
| (35) | 100 | (36) | 100 |
| (37) | 100 | (38) | 100 |
| (39) | 100 | (40) | 100 |
| (41) | 100 | (42) | 100 |
| (43) | 100 | (44) | 100 |

-continued

| Test compound | Mortality (%) | Test compound | Mortality (%) |
|---|---|---|---|
| (45) | 100 | (46) | 100 |
| (47) | 100 | (48) | 100 |
| (49) | 100 | (50) | 100 |
| (51) | 100 | (52) | 100 |
| (53) | 100 | (54) | 100 |
| (55) | 100 | (56) | 100 |
| (57) | 100 | (58) | 100 |
| (59) | 100 | (60) | 100 |
| (61) | 100 | (62) | 100 |
| (63) | 100 | (64) | 100 |
| (65) | 100 | No treatment | 0 |

EXAMPLE 8

Of the emulsifiable concentrates obtained in Preparation Example 1, those containing the present compounds (1), (5), (6), (16), (25), (31), (32), (39) and (60), respectively, were diluted 1000 times with water. The dilute liquor was sprayed on rice plants cultivated in a Wagner's pot at a rate of 15 ml per pot. After air-drying, the pot was covered with a wire-screen cage, and 15 smaller brown planthopper adults (Laodelphax striatellus) were liberated therein. In order to examine the residual effect, another group of 15 smaller brown planthopper adults were liberated therein 5 days after spraying. The dead and alive of each group were counted 24 hours after the group was liberated in the cage. The mortality is shown in the following table.

| Test compound | Liberation on the spraying day | Liberation 5 days after spraying |
|---|---|---|
| (1) | 100% | 100% |
| (5) | 100 | 100 |
| (6) | 100 | 70 |
| (16) | 100 | 70 |
| (25) | 100 | 80 |
| Diazinon* | 100 | 60 |
| No treatment | 3 | 0 |

| Test compound | Liberation on the spraying day | Liberation 5 days after spraying |
|---|---|---|
| (31) | 100% | 96% |
| (32) | 100 | 96 |
| (39) | 100 | 87 |
| (60) | 100 | 90 |
| Diazinon* | 100 | 70 |
| MPMC** | 100 | 50 |
| No treatment | 0 | 3 |

*Control: O,O-Diethyl O-(2-isopropyl-4-methyl-6-pyrimidinyl)phosphorothioate
**Control: 3,4-Xylyl N-methylcarbamate Both controls were used as a 500 ppm solution.

EXAMPLE 9

Of the emulsifiable concentrates obtained in Preparation Example 1, those containing the present compounds (31), (32), (38), (47) and (52), respectively, were each diluted 1000 times with water and sprayed on rice plants cultivated in Wagner's pots at a rate of 15 ml/pot. After air-drying, the pot was covered with a wire-screen cage, and 15 resistant green rice leafhopper adults (Nephotettix cincticeps) (Nakagawara strain) were liberated therein. In order to examine the residual effect, another group of 15 green rice leafhopper adults were liberated therein 5 days after spraying. The dead and alive of each group were counted 24 hours after the group was liberated in the cage. The mortality is shown in the following Table (2 replications).

| Test compound | Liberation on the spraying day | Liberation 5 days after spraying |
|---|---|---|
| (31) | 100% | 100% |
| (32) | 100 | 93 |
| (38) | 100 | 87 |
| (47) | 100 | 80 |
| (52) | 100 | 90 |
| Diazinon* | 63 | 7 |
| MPMC* | 80 | 0 |

*Control: Used as a 500 ppm solution.

EXAMPLE 10

Five milliliters of the oil spray obtained in Preparation Example 9 was sprayed on about 100 housefly adults (Musca domestica) per group, according to the Campbell's turntable method [Soap and Sanitary Chemicals, Vol. 14, No. 6, 119 (1938)]. The housefly adults were exposed to the descending mist for 10 minutes. By the next day, more than 80% of the houseflies could be killed with any oil spray.

EXAMPLE 11

The insecticidal activity on housefly adults (Musca domestica) of each aerosol obtained in Preparation Examples 10 and 11 was tested by the aerosol test method (Soap and Chemical Specialities, Blue Book, 1965) using a (6 ft)$^3$ Peet Grady's chamber. As a result, with any aerosol, more than 80% of the flies could be knocked down within 15 minutes after spraying, and more than 70% of the flies could be killed by the next day.

EXAMPLE 12

Each dust obtained in Preparation Example 5 was applied, by means of a Bell jar duster, on potted rice seedlings (diameter of pot, 10 cm), which had elapsed 20 days after sowing, at a rate of 2 kg/10 are under a pressure of 200 mmHg. After application, the pot was covered with a wire-screen cage, and about 20 green rice leafhopper adults (Nephotettix cincticeps) were liberated therein. After 24 hours, the dead and alive were counted, and it was found that the mortality was 100% in each case.

EXAMPLE 13

Carmine mite female adults (Tetranychus cinnabarinus) were made parasitic on the leaves of potted kidney bean (primordial leaf stage), at a rate of 10–15/leaf, which had elapsed 9 days after sowing, and bred at 27° C. for a week in a constant temperature room. Then, it was found that numerous carmine mites bred to various growth stages. At this time, a 1000-fold aqueous dilute liquor of each of the emulsifiable concentrates containing the present compounds (1), (2), (5), (13), (17), (23), (25), (29), (31), (32), (33), (34), (37), (39), (45), (47), (48), (51), (52), (56), (58) and (63), respectively, among those obtained in Preparation Example 1 was sprayed on the kidney bean at a rate of 10 ml/pot by means of a turntable. Eight days after spraying, the degree of damage of kidney bean and the number of female adults were examined (2 replications).

| Test compound | Degree of damage* | Number of female adults |
|---|---|---|
| (1) | — | 0 |
| (2) | — | 0 |
| (5) | — | 11 |
| (13) | — | 0 |
| (17) | — | 0 |
| (23) | — | 2 |
| (25) | — | 0 |
| (29) | — | 0 |
| Chlordimeform** | − to + | 21 |
| No treatment | +++ | 764 |

| Test compound | Degree of damage* | Number of female adults |
|---|---|---|
| (31) | — | 0 |
| (32) | — | 0 |
| (33) | — | 0 |
| (34) | — | 3 |
| (37) | — | 0 |
| (38) | — | 0 |
| (39) | — | 1 |
| (45) | — | 0 |
| (47) | — | 0 |
| (48) | — | 0 |
| (51) | — | 0 |
| (52) | — | 4 |
| (56) | — | 8 |
| (58) | — | 15 |
| (63) | — | 21 |
| Chlordimeform** | − to + | 29 |
| No treatment | +++ | 586 |

*Degree of damage:
−: <10%
+: 10–50%
++: 50–90%
+++: >90%
**Control: A 1000-fold aqueous-dilute liquor of a 50% emulsifiable concentrate of N'-(2-methyl-4-chlorophenyl)-N,N-dimethyl-formamidine.

EXAMPLE 14

The egg mass just before hatch of rice stem borer (*Chilo suppressalis*) was put on rice plants at the best tillering stage cultivated in a Wagner's pot. After 4 days, a 1000-fold aqueous dilute liquor of each of the emulsifiable concentrates containing the present compounds (2), (5), (17) and (25), respectively, among those obtained in Preparation Example 1 was sprayed thereon at a rate of 15 ml/pot. As a control, a 50% emulsifiable concentrate of Fenitrothion was used as a 1000-fold aqueous dilute liquor. Five days after application, the rice stem was cut to count the dead and alive of the larvae (2 replications). Water in the pot was maintained 3 cm deep throughout the test period.

| Test compound | Mortality (%) |
|---|---|
| (2) | 100 |
| (5) | 100 |
| (17) | 100 |
| (25) | 100 |
| Fenitrothion | 100 |
| No treatment | 5 |

EXAMPLE 15

Of the granules obtained in Preparation Example 6, the one containing the present compound (1) was applied, at a rate of 4 kg/10 are, to the root of rice plants at the initial tillering stage cultivated in a 1/5000 are Wagner's pot. One day after application, the pot was covered with a wire-screen cage, and about 20 smaller brown planthopper adults (*Laodelphax striatellus*) were liberated therein. Next day, the dead and alive were counted, and it was found that the mortality was 100%.

Water in the pot was maintained 3 cm deep throughout the test period.

EXAMPLE 16

Of the emulsifiable concentrates obtained in Preparation Example 1, those containing the present compounds (2) and (31), respectively, were each diluted 500 times with water. To 10 ml of the dilute liquor was added 0.5 ml of water containing numerous nematodes (*Panagrellus redivivus*). After 48 hours, the dead and alive were examined by means of a binocular microscope, and it was found that all the nematodes were killed in any treated plot.

What is claimed is:

1. A phosphoro-thioate or dithioate of the formula,

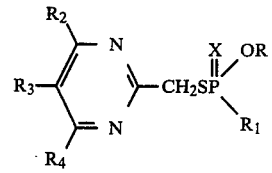

wherein R is a methyl or ethyl group, $R_1$ is a methoxy, ethoxy, methylamino or ethylamino group, $R_2$ is a halogen atom, or a $C_1$–$C_3$ alkyl group, $R_3$ is a hydrogen atom, $R_4$ is a $C_1$–$C_3$ alkyl group and X is an oxygen or sulfur atom, provided X is an oxygen atom when $R_1$ is a methylamino or ethylamino group.

2. O,O-Dimethyl S-(4-chloro-6-methylpyrimidin-2-ylmethyl)phosphorodithioate.

3. O,O-Dimethyl S-(4,6-dimethylpyrimidin-2-ylmethyl)phosphorodithioate.

4. O,O-Diethyl S-(4-chloro-6-methylpyrimidin-2-ylmethyl)phosphorodithioate.

5. O,O-Diethyl S-(4,6-dimethylpyrimidin-2-ylmethyl)phosphorodithioate.

6. O-Methyl S-(4,6-dimethylpyrimidin-2-ylmethyl) N-methylphosphoroamidothioate.

7. O-Methyl S-(4,6-dimethylpyrimidin-2-ylmethyl) N-ethylphosphoroamidothioate.

* * * * *